(12) United States Patent
Clasen

(10) Patent No.: US 12,702,750 B2
(45) Date of Patent: Aug. 11, 2026

(54) FLUID TRANSFER SYSTEM FOR DRUG DELIVERY DEVICE

(71) Applicant: Becton, Dickinson and Company, Franklin Lakes, NJ (US)

(72) Inventor: Eric Scott Clasen, Hillsborough, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 634 days.

(21) Appl. No.: 18/023,557

(22) PCT Filed: Aug. 31, 2021

(86) PCT No.: PCT/US2021/048345
§ 371 (c)(1),
(2) Date: Feb. 27, 2023

(87) PCT Pub. No.: WO2022/047355
PCT Pub. Date: Mar. 3, 2022

(65) Prior Publication Data

US 2023/0310738 A1 Oct. 5, 2023

Related U.S. Application Data

(60) Provisional application No. 63/072,625, filed on Aug. 31, 2020.

(51) Int. Cl.
*A61M 5/142* (2006.01)
*A61M 5/145* (2006.01)

(52) U.S. Cl.
CPC ...... *A61M 5/14248* (2013.01); *A61M 5/1454* (2013.01); *A61M 2005/14252* (2013.01)

(58) Field of Classification Search
CPC ............ A61M 5/14248; A61M 5/1454; A61M 2005/14252
See application file for complete search history.

(56) References Cited

U.S. PATENT DOCUMENTS 8,382,713 B2 2/2013 Glynn
10,603,445 B2 3/2020 Quinn et al.
2012/0215183 A1* 8/2012 Halili .................... A61M 39/24 604/257
2017/0028132 A1* 2/2017 Cronenberg ...... A61M 5/31568
2017/0354788 A1 12/2017 Quinn et al.
2020/0376195 A1* 12/2020 Falkovich ........... A61M 5/1454

* cited by examiner

*Primary Examiner* — James D Ponton
(74) *Attorney, Agent, or Firm* — The Webb Law Firm

(57) ABSTRACT

A valve assembly for a drug delivery includes a valve housing having a first side and a second side positioned opposite from the first side, a cannula having a first end and a second end positioned opposite the first end, with the cannula defining a central passageway, and a valve sleeve defining a cannula space. The valve sleeve is configured to move from a pre-use position where the first end of the cannula is received within the cannula space to a use position where the first end of the cannula extends outside of the valve sleeve and the cannula space. The valve sleeve is configured to contact a container of the drug delivery device before any other element of the valve assembly when the valve sleeve moves from a pre-use position to the use position.

15 Claims, 15 Drawing Sheets

10
12
32
34
14
106
118
16
18
24

10
12
102
42
34
106
14
36
104
116
16
112
108
18
110
114
24

FLUID TRANSFER SYSTEM FOR DRUG DELIVERY DEVICE

CROSS-REFERENCE TO RELATED APPLICATION

The present application is the United States national phase of International Application No. PCT/US2021/048345 filed Aug. 31, 2021, and claims priority to U.S. Provisional Application Ser. No. 63/072,625, entitled "Fluid Transfer System for Drug Delivery Device", filed Aug. 31, 2020, the entire disclosures of which are hereby incorporated by reference in their entirety.

BACKGROUND OF THE INVENTION

Field of the Invention

The present disclosure relates generally to a drug delivery device and, in particular, to a fluid transfer system for a drug delivery device.

Description of Related Art

Various types of automatic injection or drug delivery devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

In one aspect or embodiment, a valve assembly for a drug delivery device includes a valve housing having a first side and a second side positioned opposite from the first side, a cannula having a first end and a second end positioned opposite the first end, with the cannula defining a central passageway, and a valve sleeve defining a cannula space.

The valve sleeve is configured to move from a pre-use position where the first end of the cannula is received within the cannula space to a use position where the first end of the cannula extends outside of the valve sleeve and the cannula space. The valve sleeve is configured to contact a container of the drug delivery device before any other element of the valve assembly when the valve sleeve moves from the pre-use position to the use position.

The valve sleeve may be secured to the valve housing. An outermost portion of the valve sleeve may be secured to the valve housing. The valve sleeve may be secured to the valve housing via a retainer engaged with the valve sleeve and the valve housing. The valve housing may include a projection engaged with the retainer.

The valve sleeve may include a first cylindrical portion having a convex tip, a second portion extending from the first portion, and a third frustoconical portion extending from the second portion. The second portion of the valve sleeve may be a frustoconical section and a cylindrical section. The third portion of the valve sleeve may include at least one recessed portion configured to facilitate a collapse and deformation of the valve sleeve. The valve sleeve may be formed from an elastomeric material.

In one aspect or embodiment, a drug delivery device includes a housing and a container received within the housing, with the container having a first end and a second end positioned opposite the first end. The container includes a barrel having a first end and a second end positioned opposite the first end and configured to receive a medicament, a stopper moveable within the barrel to dispense the medicament from the barrel, and a septum received by the second end of the barrel and having a first side and a second side positioned opposite the first side. The container defines an open space extending from the second side of the septum to the second end of the container. The drug delivery device further includes a drive assembly received within the housing and configured to engage the container and dispense medicament from the container, a needle actuator assembly received within the housing, with the needle actuator assembly comprising a patient needle configured to pierce a patient's skin, and a valve assembly according to any of the aspects or embodiments discussed above.

The valve sleeve may engage the septum of the container when the valve sleeve moves from the pre-use position to the use position. The container may further include a locking element having a main body and a locking ring, with the locking element configured to secure the septum to the barrel of the container.

In one aspect or embodiment, a method of packaging and sterilizing the drug delivery device according to any of the aspects or embodiments discussed above includes: a) sterilizing and positioning the barrel and septum of the container in a first package; b) sterilizing and positioning the stopper of the container in a second package; c) sterilizing and positioning the housing, drive assembly, needle actuator assembly, and the valve assembly in at least a third package; d) filling the container with medicament; e) assembling the drug delivery device and positioning the drug delivery device in a fourth package; and f) after step e), sterilizing the drug delivery device.

The sterilizing of step f) may include a vaporized peracetic acid sterilization process. The fourth package may be formed from a porous material.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION

Figure 1:
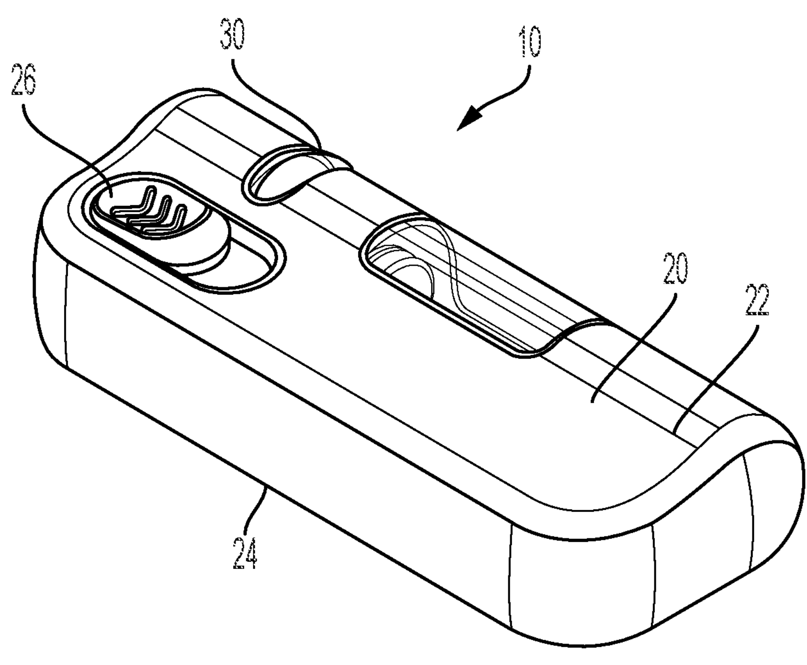
FIG. 1 is a perspective view of a drug delivery system according to one aspect or embodiment of the present application.
Figure 2:
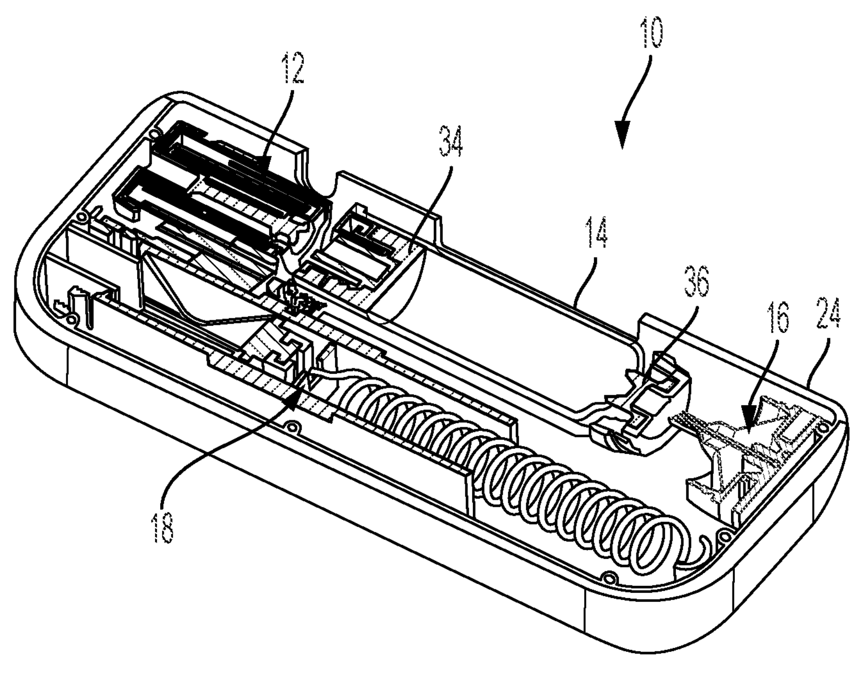
FIG. 2 is a perspective, cross-sectional view of the drug delivery system of FIG. 1.
Figure 3:
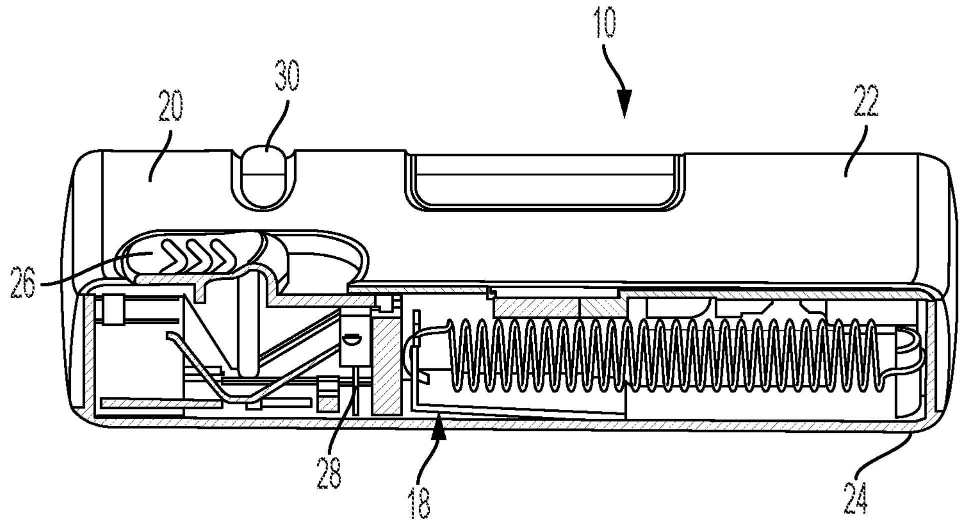
FIG. 3 is a front, cross-sectional view of the drug delivery system of FIG. 1.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-16, a drug delivery device 10 includes a drive assembly 12, a container 14, a valve assembly 16, and a needle actuator assembly 18. The drive assembly 12, the container 14, the valve assembly 16, and the needle actuator assembly 18 are at least partially positioned within a housing 20. The housing 20 includes a top portion 22 and a bottom portion 24, although other suitable arrangements for the housing 20 may be utilized. In one aspect, the drug delivery device 10 is an injector device configured to be worn or secured to a user and to deliver a predetermined dose of a medicament provided within the container 14 via injection into the user. The device 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The device 10 may deliver the medicament at a fixed pressure to the user with the rate being variable. The general operation of the device 10 is described below in reference to FIGS. 1-16.

Referring again to FIGS. 1-16, the device 10 is configured to operate through the engagement of an actuation button 26 by a user, which results in a needle 28 of the needle assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. The operation of the device 10 is also shown and described in U.S. Publication No. 2017/0354788, which is hereby incorporated by reference in its entirety. The housing 20 of the device 10 includes an indicator window 30 for viewing an indicator arrangement 32 configured to provide an indication to a user on the status of the device 10 and for viewing the container 14. The indicator window 30 may be a magnifying lens for providing a clear view of the indicator arrangement 32. The indicator arrangement 32 moves along with the needle actuator assembly 18 during use of the device 10 to indicate a pre-use status, use status, and post-use status of the device 10. The indicator arrangement 32 provides visual indicia regarding the status, although other suitable indicia, such an auditory or tactile, may be provided as an alternative or additional indicia.

Figure 4:
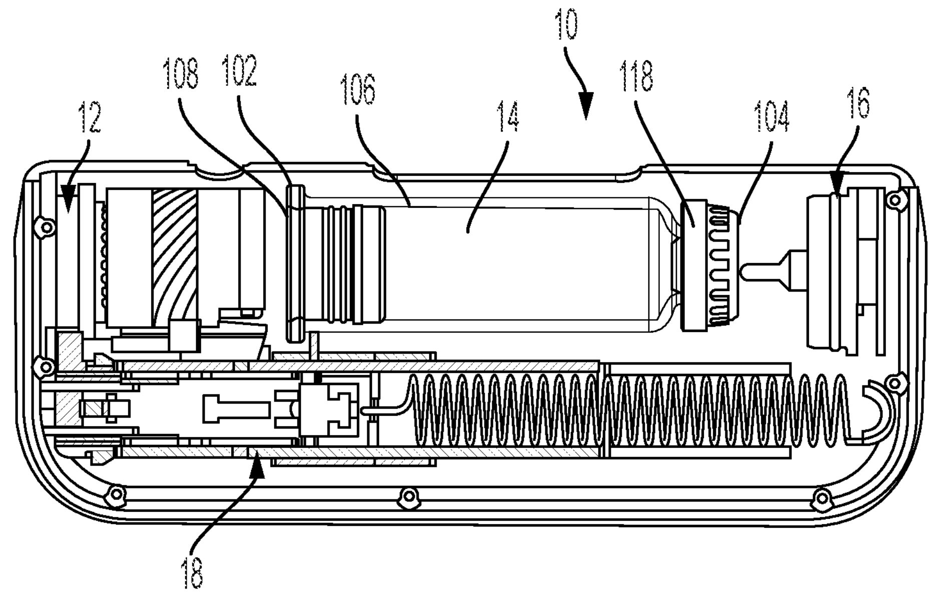
FIG. 4 is a top view of the drug delivery system of FIG. 1, showing a top portion of the housing removed and the drug delivery system in a pre-use position.
Figure 5:
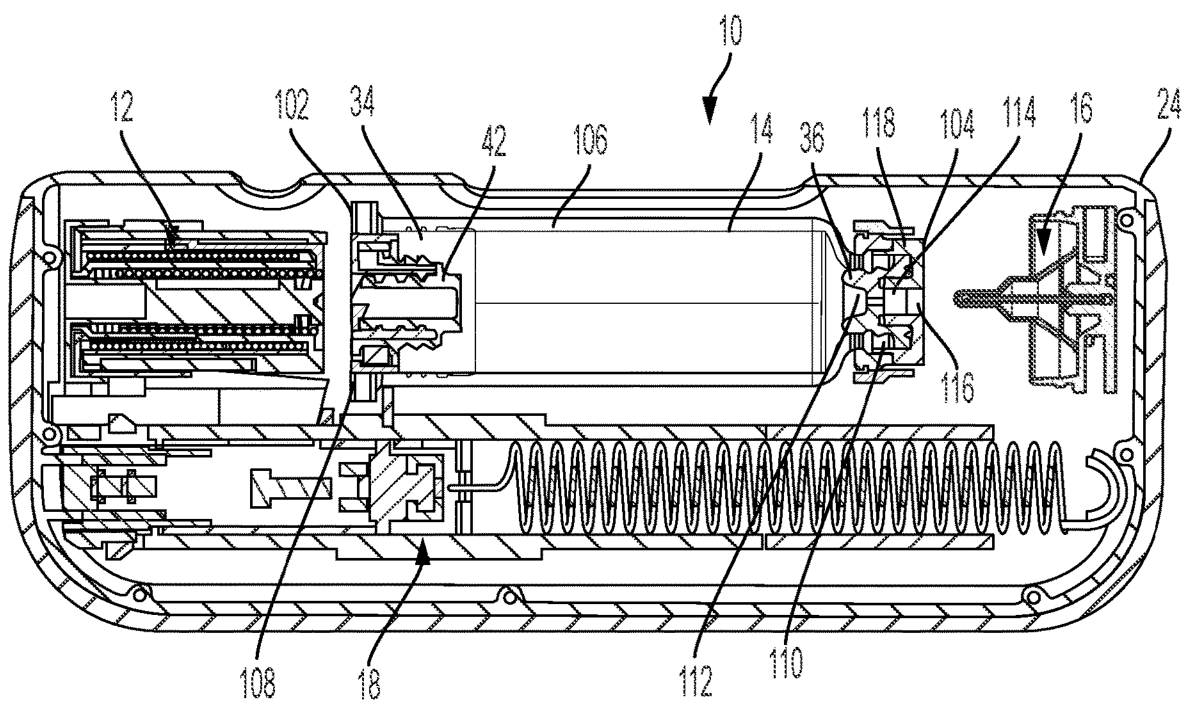
FIG. 5 is a top, cross-sectional view of the drug delivery system of FIG. 1, showing the drug delivery system in a pre-use position.
Figure 6:
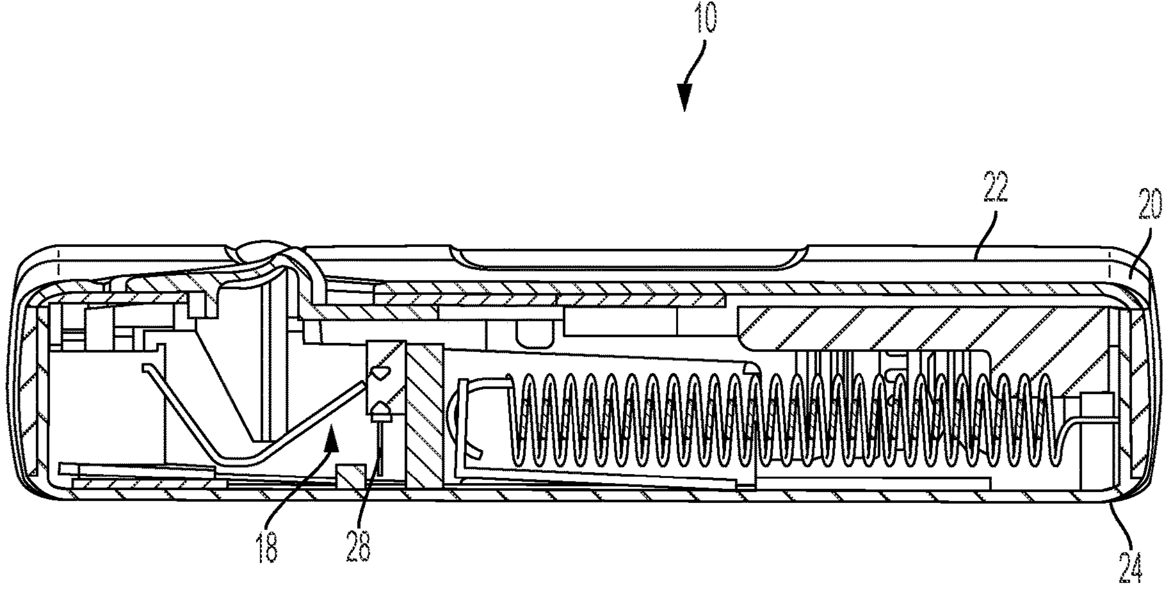
FIG. 6 is a front, cross-sectional view of the drug delivery system of FIG. 1, showing the drug delivery system in a pre-use position.
Figures 7, 8:
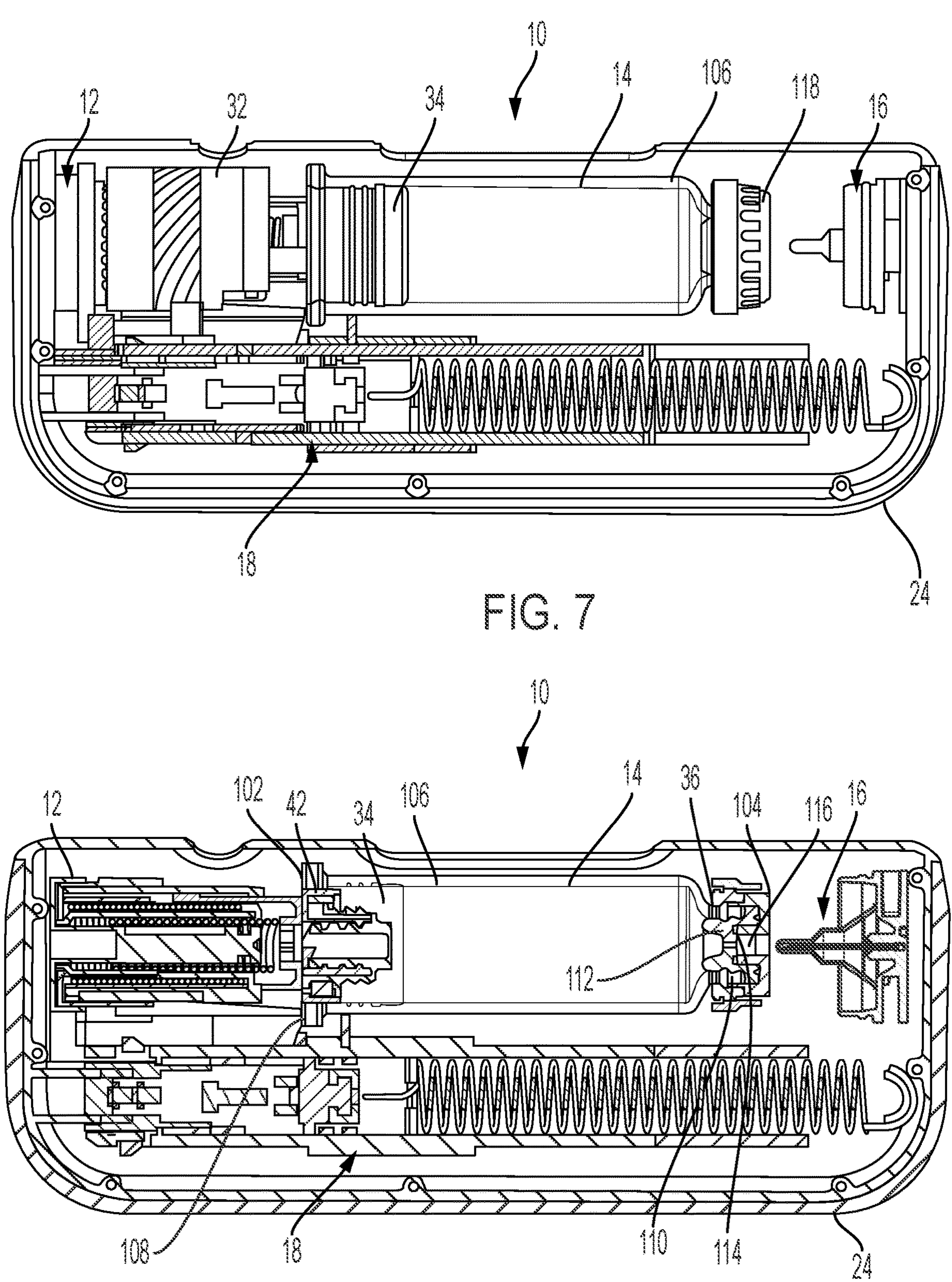
FIG. 7 is a top view of the drug delivery system of FIG. 1, showing a top portion of the housing removed and the drug delivery system in an initial actuation position.
FIG. 8 is a top, cross-sectional view of the drug delivery system of FIG. 1, showing the drug delivery system in an initial actuation position.
Figure 9:
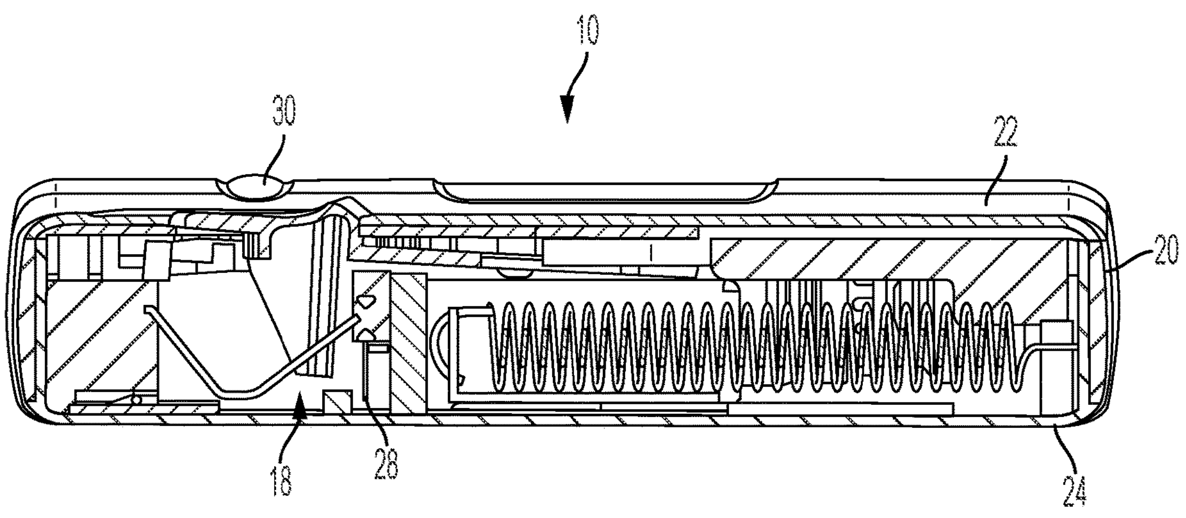
FIG. 9 is a front, cross-sectional view of the drug delivery system of FIG. 1, showing the drug delivery system in an initial actuation position.

Referring to FIGS. 4-6, during a pre-use position of the device 10, the container 14 is spaced from the drive assembly 12, and the valve assembly 16 and the needle 28 is in a retracted position. During the initial actuation of the device 10, as shown in FIGS. 7-9, the drive assembly 12 engages the container 14 to move the container 14 toward the valve assembly 16, which is configured to pierce a septum 36 of the container 14 and place the medicament within the container 14 in fluid communication with the needle 28 via a tube (not shown) or other suitable arrangement. The drive assembly 12 is configured to engage a stopper 34 of the container 14 or a spacer assembly 42 engaged with the stopper 34, which will initially move the entire container 14 into engagement with the valve assembly 16 due to the incompressibility of the fluid or medicament within the container 14. The initial actuation of the device 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the device 10.

Figure 10:
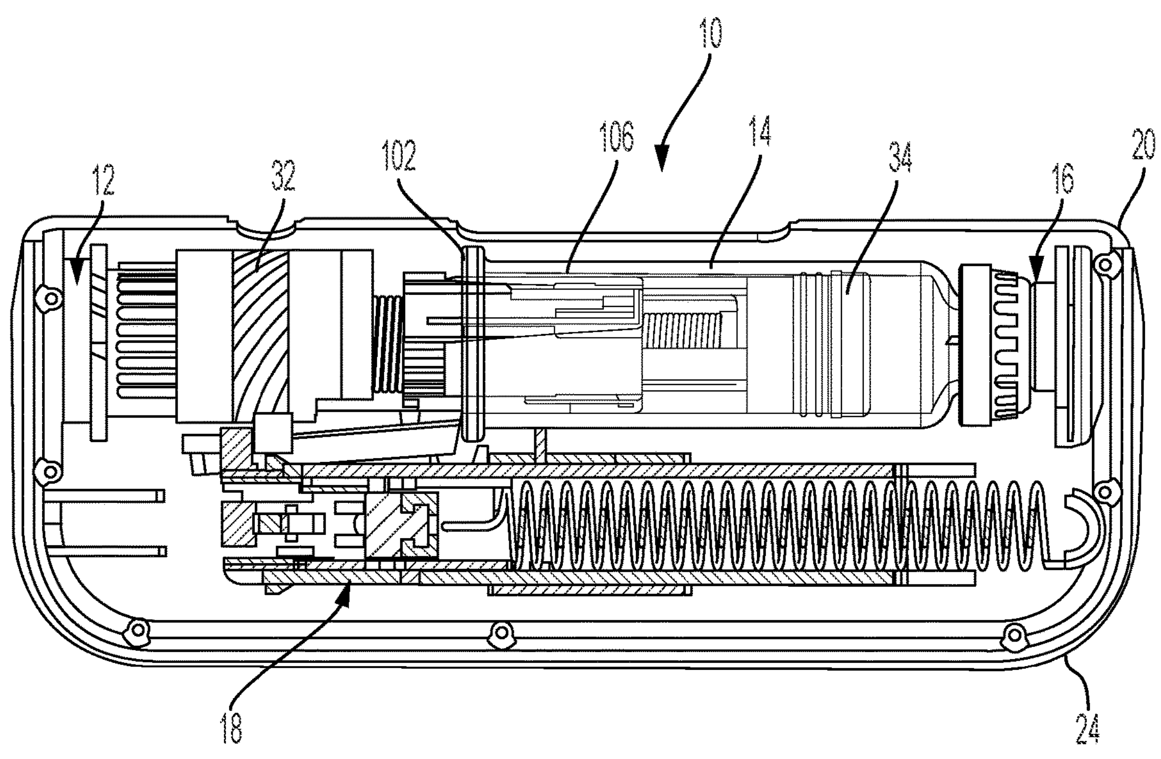
FIG. 10 is a top view of the drug delivery system of FIG. 1, showing a top portion of the housing removed and the drug delivery system in a use position.
Figure 11:
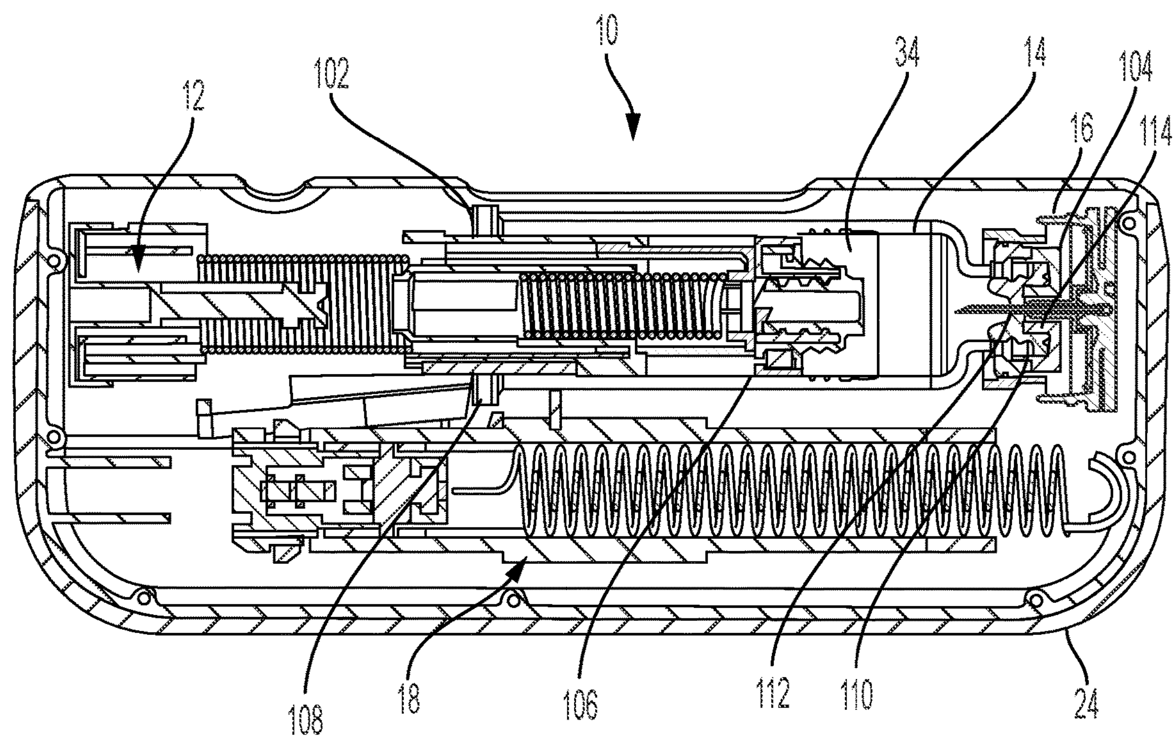
FIG. 11 is a top, cross-sectional view of the drug delivery system of FIG. 1, showing the drug delivery system in a use position.
Figure 12:
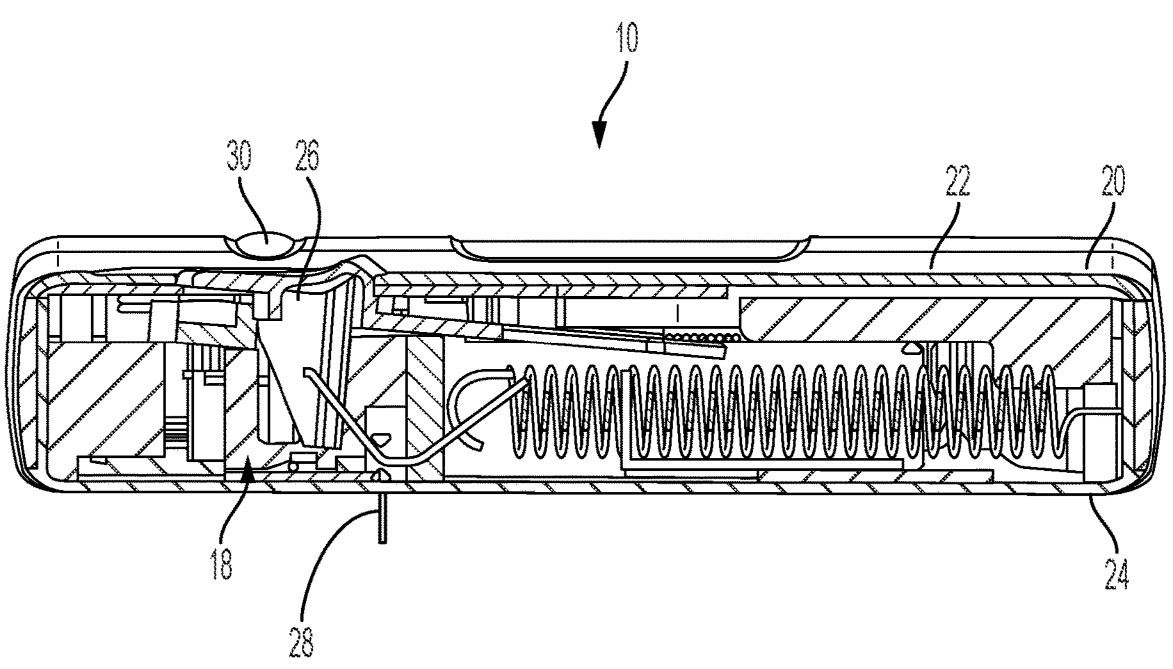
FIG. 12 is a front, cross-sectional view of the drug delivery system of FIG. 1, showing the drug delivery system in a use position.
Figure 13:
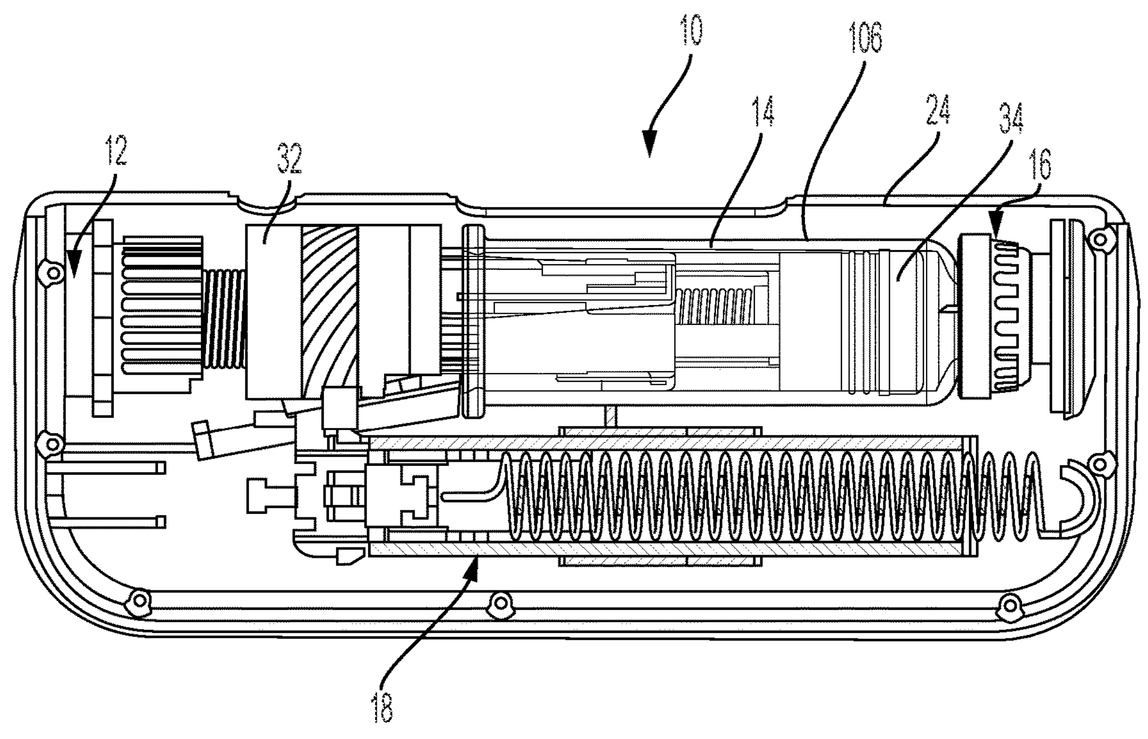
FIG. 13 is a top view of the drug delivery system of FIG. 1, showing a top portion of the housing removed and the drug delivery system in a post-use position.
Figure 14:
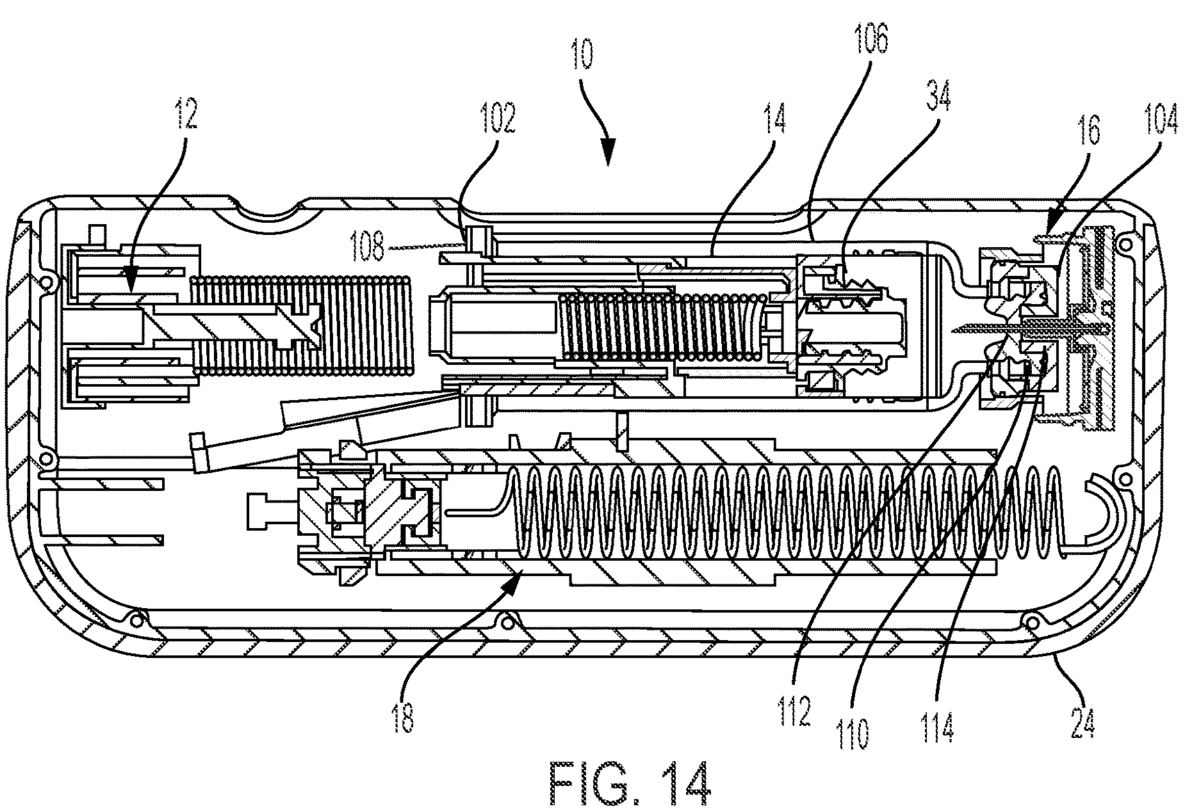
FIG. 14 is a top, cross-sectional view of the drug delivery system of FIG. 1, showing the drug delivery system in a post-use position.
Figure 15A:
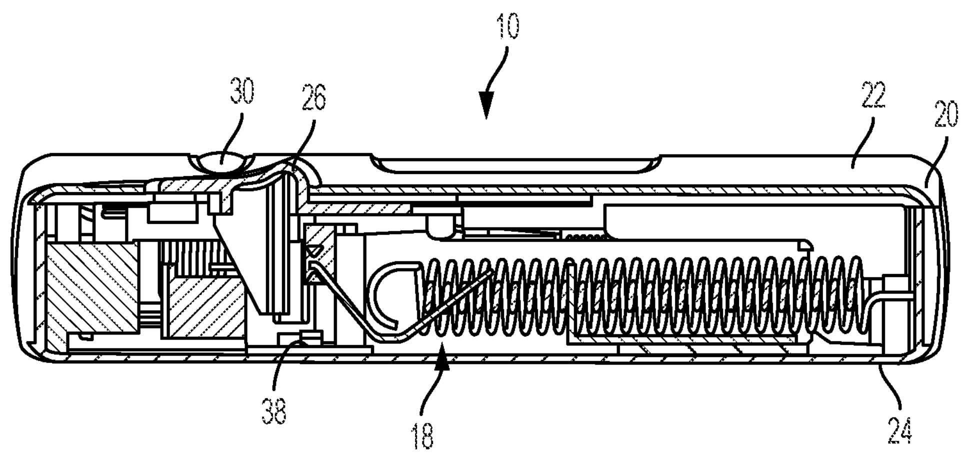
FIG. 15A is a front, cross-sectional view of the drug delivery system of FIG. 1, showing the drug delivery system in a post-use position.
Figure 15B:
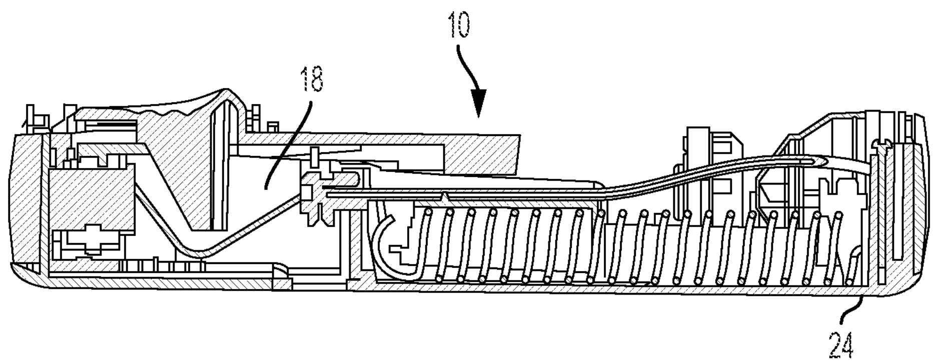
FIG. 15B is a front, cross-sectional view of the drug delivery system of FIG. 1, showing a pad with the drug delivery system in a pre-use position.
Figure 15C:
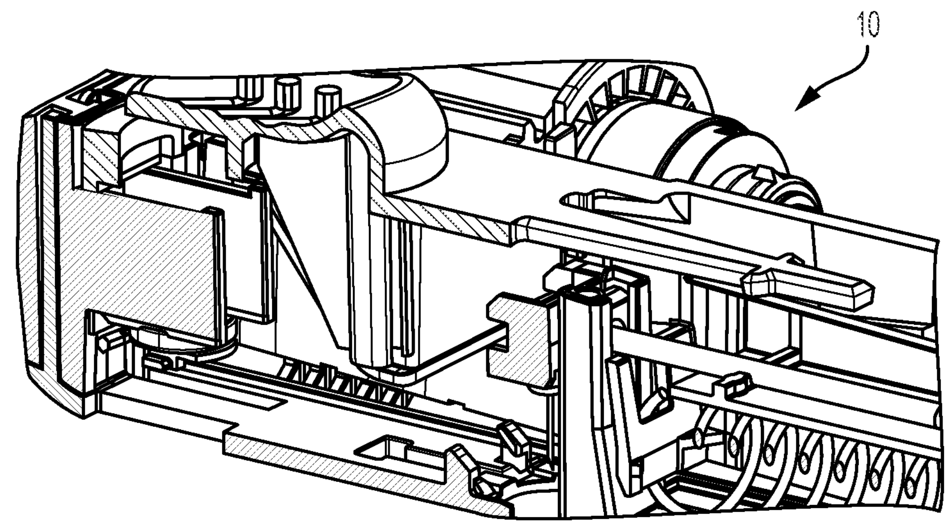
FIG. 15C is a perspective, cross-sectional view of the drug delivery system of FIG. 1, showing a pad with the drug delivery system in a pre-use position.

During the use position of the device 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced the septum 36 of the container 14 to place the container 14 in fluid communication with the needle 28, which also allows the drive assembly 12 to move the stopper 34 relative to the container 14 since fluid is able to be dispensed from the container 14. At the post-use position of the device 10, shown in FIGS. 13-15, the needle 28 is in the retracted position and engaged with a pad 38 to seal the needle 28 and prevent any residual flow of fluid or medicament from the container 14.

Figure 16:
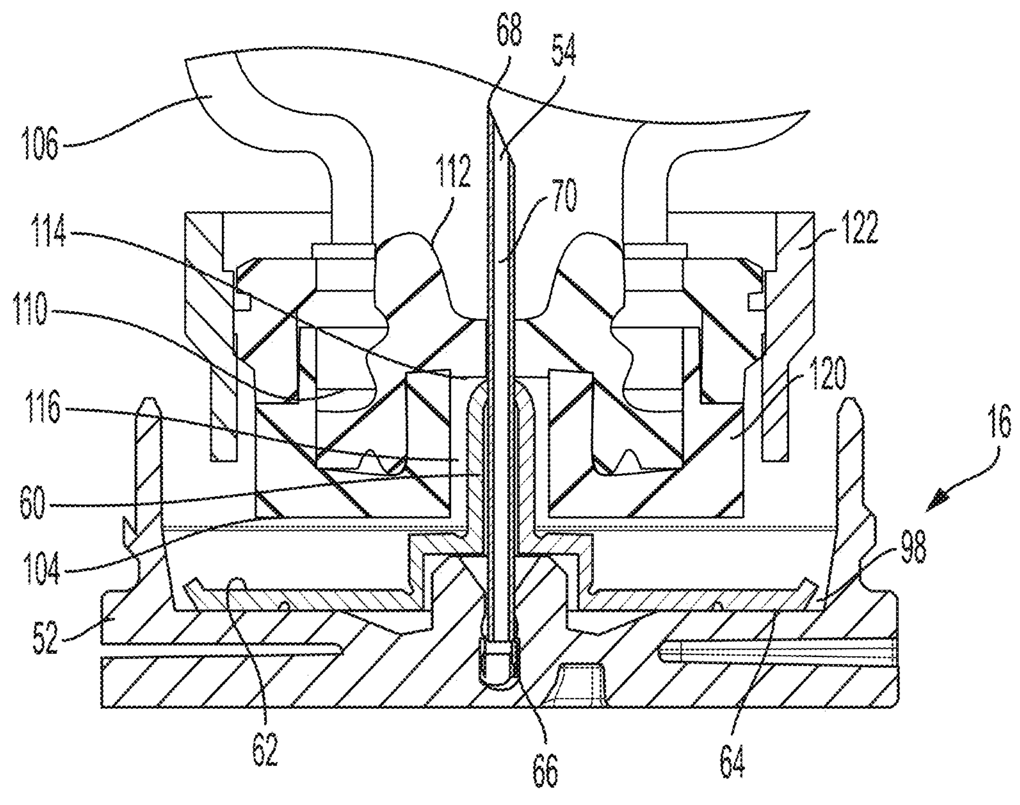
FIG. 16 is a partial cross-sectional view of the drug delivery system of FIG. 1, showing a valve assembly.
Figure 18:
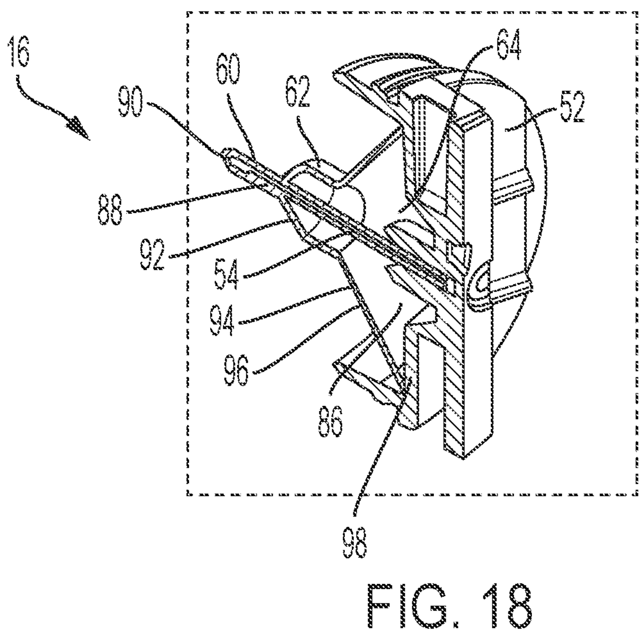
FIG. 18 is a perspective view of a valve assembly of the drug delivery system of FIG. 1.

Referring to FIGS. 16 and 18, as discussed above, the valve assembly 16 operates to facilitate fluid communication between the container 14 and the needle actuator assembly 18. The valve assembly 16 includes a valve housing 52, a cannula 54, and a valve sleeve 60. The valve sleeve has a first side 62 and a second side 64 positioned opposite from the first side 62. The valve housing 52 may be formed integrally with the housing 20 of the device 10 or may be formed as a separate component. The cannula 54 has a first end 66 and a second end 68 positioned opposite from the first end 66. The cannula 54 defines a central passageway 70. The second end 68 of the cannula 54 is sharp and configured to pierce the septum 36 of the container 14. The first end 66 of the cannula 54 is received by and secured to the valve housing 52. The valve housing 52 is in fluid communication with the needle actuator assembly 18 via tubing (not shown) to form a fluid flow path from the cannula 54 to the needle actuator assembly 18. In one aspect or embodiment, the valve assembly 16 only includes the valve housing 52, cannula 54, and the valve sleeve 60 with no other elements or components forming a part of the valve assembly 16.

Referring again to FIGS. 16 and 18, the valve sleeve 60 defines a cannula space 86 and is configured to move from a pre-use position where the second end 68 of the cannula 54 is received within the cannula space 86 to a use position where the second end 68 of the cannula 54 extends outside of the valve sleeve 60 and the cannula space 86. The valve sleeve 60 may be formed from an elastomeric material, such as a rubber material, although other suitable materials or combination of materials may also be utilized. The valve sleeve 60 is configured to contact the container 14 before any other element of the vale assembly 16 when the valve sleeve 60 moves from the pre-use position to the use position. The valve sleeve 60 includes a first cylindrical portion 88 having a convex tip 90, a second portion 92 extending from the first portion 88, and a third frustoconical portion 94 extending from the second portion 92. The second portion 92 is frustoconical and cylindrical. The third portion 94 of the valve sleeve 60 may include one or more recessed portions 96 to facilitate the collapse and deformation of the valve sleeve 60. In one aspect or embodiment, after actuation of the drug delivery device 10, the drive assembly 12 moves the container 14 until the valve sleeve 60 engages the septum 36 of the container 14, which causes the valve sleeve 60 to move from the pre-use position to the use position such that the cannula 54 pierces the septum 36 of the container 14 to place the medicament in the container in fluid communication with the cannula 54. The valve sleeve 60 is configured to ensure the cannula 54 and flow path of the device 10 remain free from contamination during operation of the device 10.

In one aspect or embodiment, an outermost portion 98 of the valve sleeve 60 is secured to the valve housing 52. The outermost portion 98 of the valve sleeve 60 may be secured to the valve housing 52 via an adhesive, fastener, or other suitable arrangement. In one aspect or embodiment, the valve sleeve 60 is secured to the valve housing 52 via a locking engagement between the valve sleeve 60 and valve housing 52, as discussed in more detail below.

Figure 17:
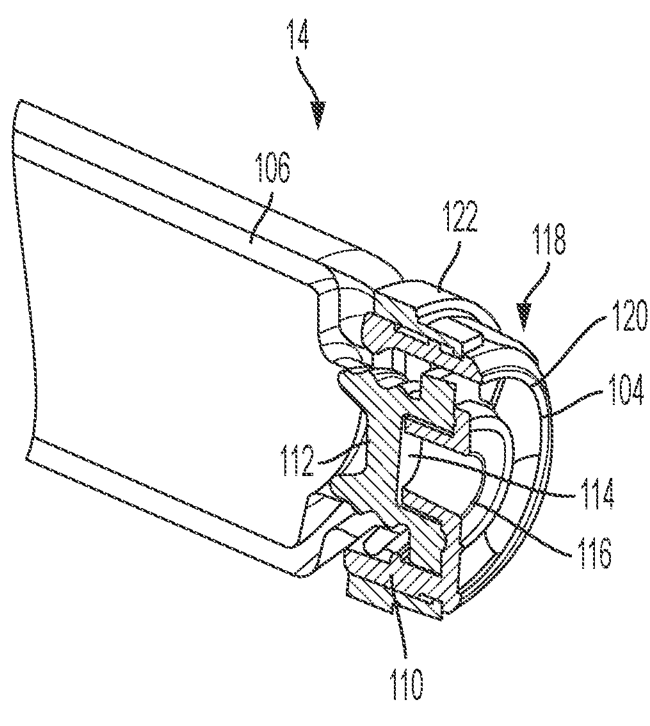
FIG. 17 is a partial cross-sectional view of a container of the drug delivery system of FIG. 1.

Referring to FIGS. 4, 5 and 17, the container 14 has a first end 102 and a second end 104 positioned opposite the first end 102. The container 14 includes a barrel 106 having a first end 108 and a second end 110 positioned opposite the first end 108, with the barrel 106 configured to receive a medicament. The container 14 includes the stopper 34, which is moveable within the barrel 106 to dispense the medicament from the barrel 106, and the septum 36 received by the second end 110 of the barrel 106. The septum 36 has a first side 112 and a second side 114 positioned opposite the first side 112. The container 14 defines an open space 116 extending from the second side 114 of the septum 36 to the second end 104 of the container 14. The valve sleeve 60 is configured to directly contact the second side 114 of the septum 36 when the valve sleeve 60 moves from the pre-use position to the post-use position. The container 14 also includes a locking element 118 having a main body 120 and a locking ring 122. The locking element 118 is configured to secure the septum 36 to the barrel 106 of the container 14. In one aspect or embodiment, the container 14 does not include any seals, such as a foil seal, that covers a portion of the septum 36 or a portion of the locking element 118.

Figure 19:
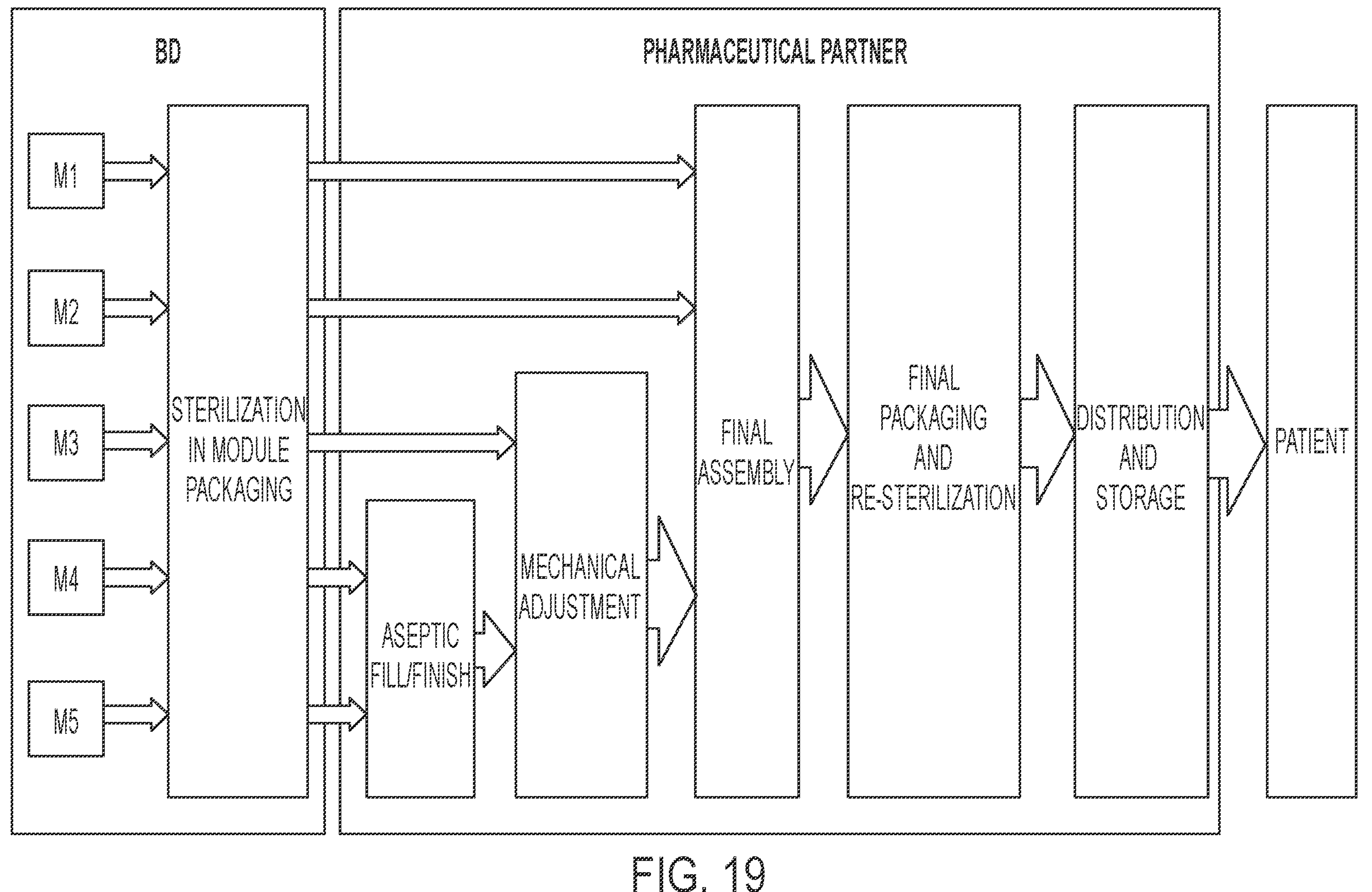
FIG. 19 is a flow chart of a method of assembling and sterilizing the drug delivery device of FIG. 1 according to one aspect or embodiment of the present application.

Referring to FIG. 19, in a further aspect or embodiment of the present application, a method of packaging and sterilizing the drug delivery device 10 includes: a) sterilizing and positioning the barrel 106 and septum 36 of the container 14 in a first package; b) sterilizing and positioning the stopper 34 of the container 14 in a second package; c) sterilizing and positioning the housing 20, drive assembly 12, needle actuator assembly 18, and the valve assembly 16 in at least a third package; d) filling the container 14 with medicament; e) assembling the drug delivery device 10 and positioning the drug delivery device 10 in a fourth package; and f) after step e), sterilizing the drug delivery device 10.

The sterilizing of step f) may be performed using a vaporized peracetic acid sterilization process, although other suitable sterilization processes may be utilized. The fourth package may be formed from a porous material to allow sterilization of the assembled device 10 to be sterilization after packaging. In one aspect or embodiment, the sterilizing of step f) is performed using a vaporized peracetic acid sterilization process, a nitrogen dioxide sterilization process, a vaporized hydrogen peroxide process, and/or an ethylene oxide sterilization process. In one aspect or embodiment, the fourth package, as well as the first, second, and third packages, may be formed, in part, from a non-woven high density polyethylene fiber material, such Tyvek® commercially available from DuPont. Other packaging options include a pouch or tray made from plastic, such as polyethylene, a laminate of multiple polymers, such as polyethylene terephthalate glycol, optionally with a breathable portion made, for example, from Tyvek®. In one aspect or embodiment, step (e) includes positioning the drug delivery device 10 is a clam shell tray and then positioning the drug delivery device 10 and clam shell into a pouch, where the clam shell and the pouch may be formed from Tyvek®.

In one aspect or embodiment, the method includes separately sterilizing and packaging the top portion 22 of the housing 20 for later assembly with the other components. The spacer assembly 42 may also be separately sterilized and packaged for later assembly with the other components.

In one aspect or embodiment, prior to assembling the drug delivery device, the method includes a mechanical adjustment, such as adjusting the spacer assembly 42 and/or the fit of the various components.

In one aspect or embodiment, the method further includes performing a mechanical sterility maintenance test, such as a pressure decay test or dye test.

Figure 20:
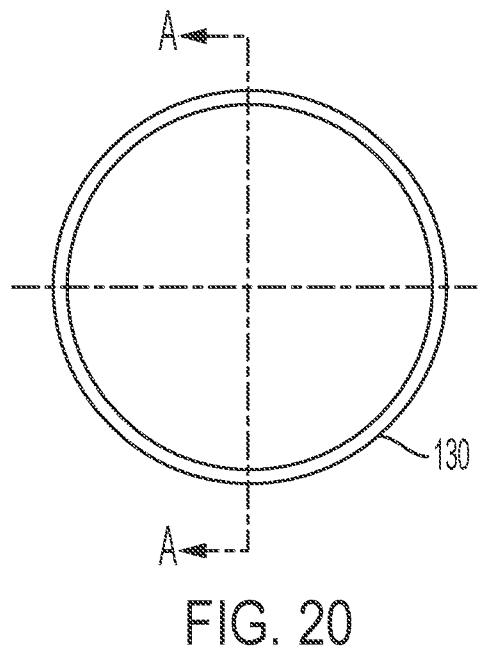
FIG. 20 is a top view of a retainer of a valve assembly according to one aspect or embodiment of the present application.
Figure 21:
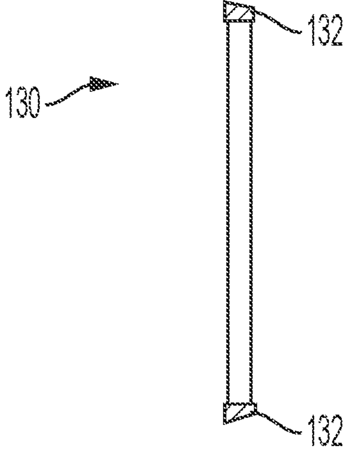
FIG. 21 is a cross-sectional view along line A-A shown in FIG. 20.
Figure 22:
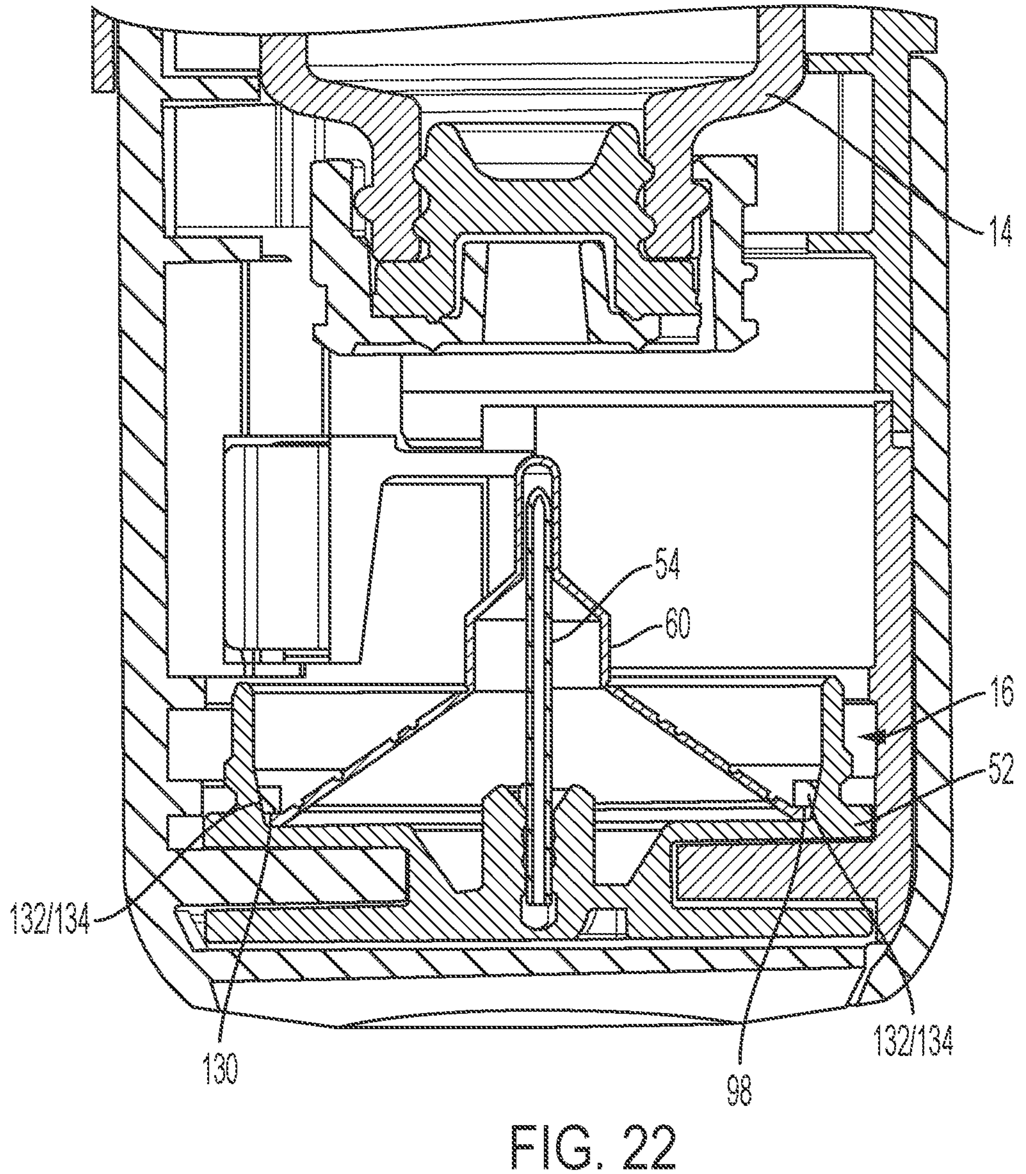
FIG. 22 is a partial cross-sectional view of a drug delivery system according to a further aspect or embodiment of the present application.

Referring to FIGS. 20-22, a retainer 130 for the valve assembly 16 of the drug delivery device 10 according to one aspect or embodiment is shown. The retainer 130 is ring-shaped, although other suitable shapes may be utilized. The retainer 130 includes a tapered outer surface 132 that is configured to engage a corresponding tapered surface 134 of the valve housing 52. As shown in FIG. 22, the retainer 130 is positioned in the valve housing 52 with the tapered outer surface 132 engaging the tapered surface 134 of the valve housing 52 with the retainer 130 engaging the outermost portion 98 of the valve sleeve 60 to secure the valve sleeve 60 to the valve housing 52.

Figure 23:
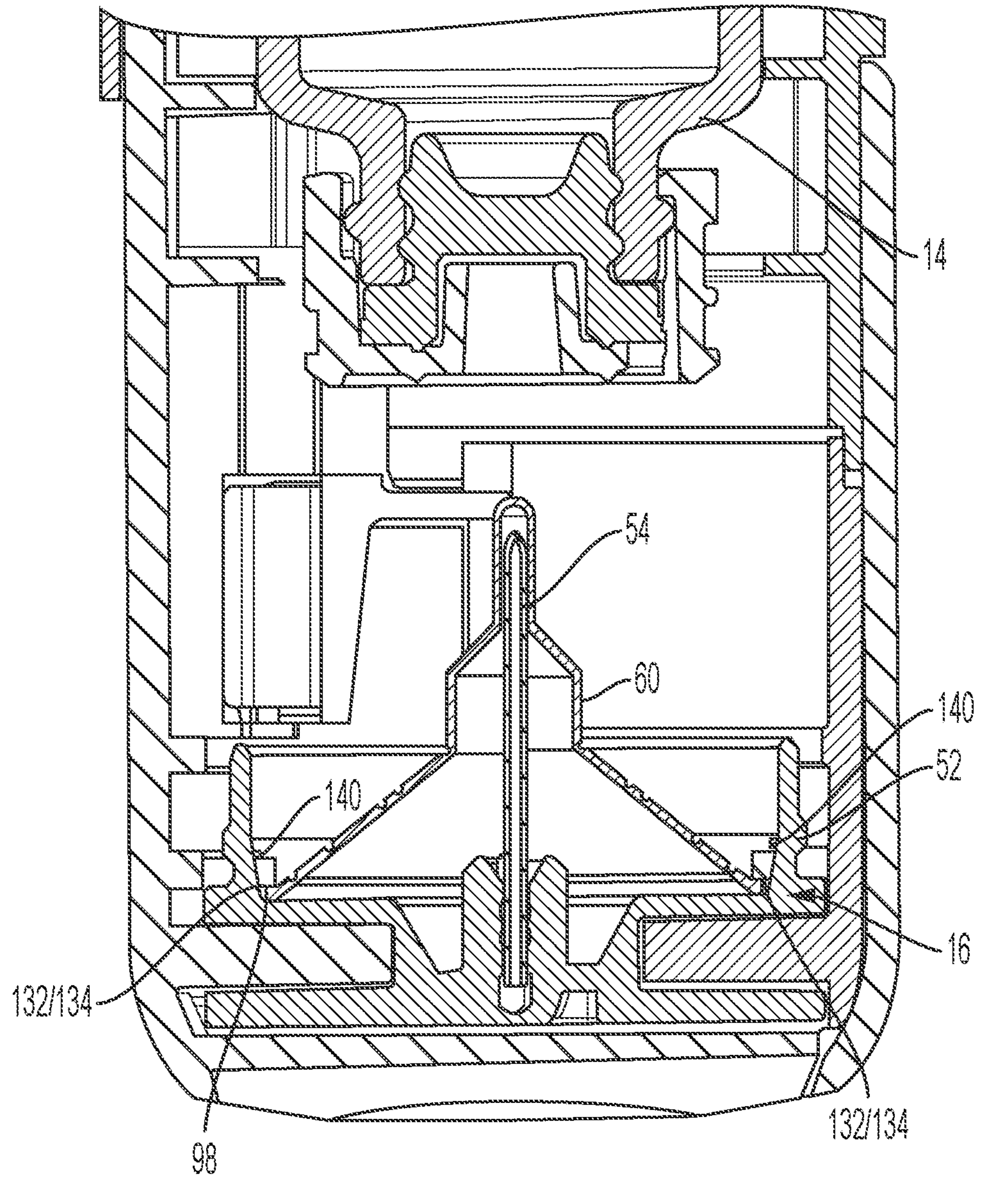
FIG. 23 is a partial cross-sectional view of a drug delivery system according to a further aspect or embodiment of the present application.

Referring to FIG. 23, in one aspect or embodiment, the valve housing 52 further includes a projection 140 extending radially inward from the valve housing 52. The projection 140 is configured to engage and hold the retainer 130 in place once the retainer 130 has been fully inserted into the valve housing 52. The projection 140 may be a continuous ring or may be one or more projections.

Figure 24:
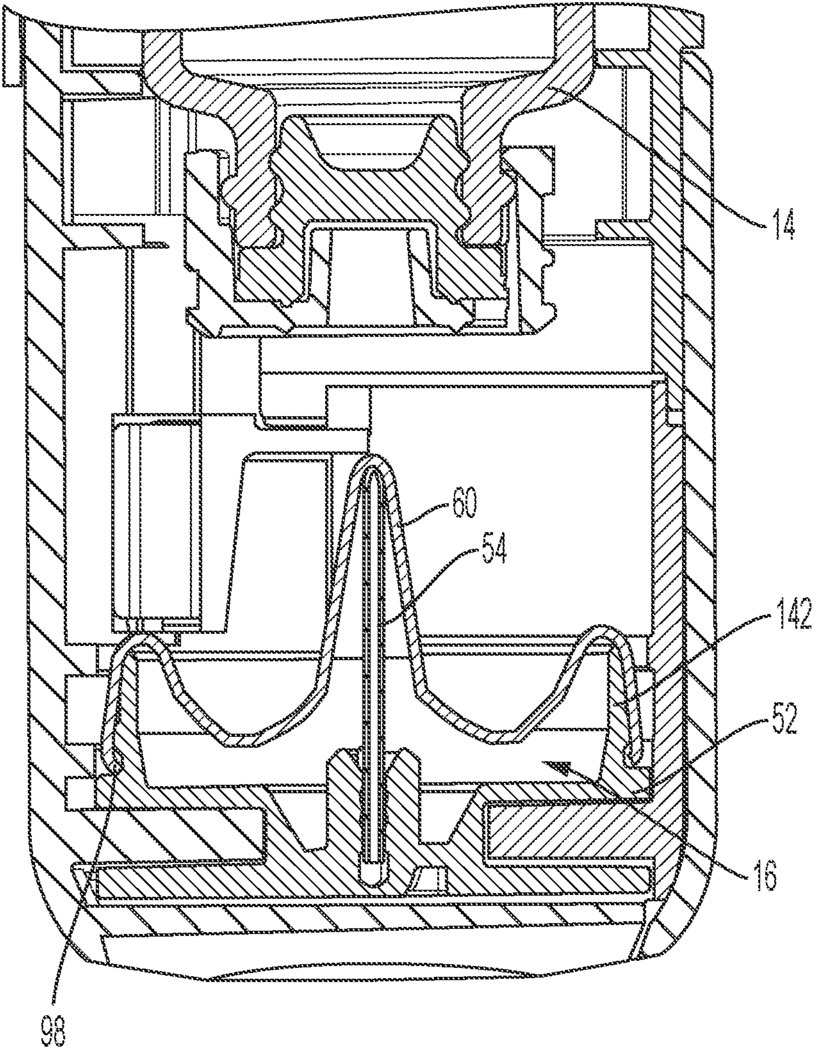
FIG. 24 is a partial cross-sectional view of a drug delivery system according to a further aspect or embodiment of the present application.

Referring to FIG. 24, rather than securing the outermost portion 98 of the valve sleeve 60 within the valve housing 52, in one aspect or embodiment, the outermost portion 98 of the valve sleeve 60 is secured to an outer surface 142 of the valve housing 52. The valve sleeve 60 may be secured to the out surface 142 via engagement with a portion of the valve housing 52, adhesive, fastener, the retainer 130, or any other suitable arrangement.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A valve assembly for a drug delivery device, the valve assembly comprising:

a valve housing having a first side and a second side positioned opposite from the first side;

a cannula having a first end and a second end positioned opposite the first end, the cannula defining a central passageway; and a valve sleeve defining a cannula space, the valve sleeve is configured to move from a pre-use position where the first end of the cannula is received within the cannula space to a use position where the first end of the cannula extends outside of the valve sleeve and the cannula space, wherein the valve sleeve is configured to contact a container of the drug delivery device before any other element of the valve assembly when the valve sleeve moves from the pre-use position to the use position, wherein the valve sleeve comprises a first cylindrical portion having a convex tip, a second portion extending from the first portion, and a third frustoconical portion extending from the second portion.

2. The valve assembly of claim 1, wherein the valve sleeve is secured to the valve housing.

3. The valve assembly of claim 2, wherein an outermost portion of the valve sleeve is secured to the valve housing.

4. The valve assembly of claim 2, wherein the valve sleeve is secured to the valve housing via a retainer engaged with the valve sleeve and the valve housing.

5. The valve assembly of claim 4, wherein the valve housing comprises a projection engaged with the retainer.

6. The valve assembly of claim 1, wherein the second portion of the valve sleeve comprises a frustoconical section and a cylindrical section.

7. The valve assembly of claim 1, wherein the third portion of the valve sleeve comprises at least one recessed portion configured to facilitate a collapse and deformation of the valve sleeve.

8. The valve assembly of claim 1, wherein the valve sleeve comprises an elastomeric material.

9. The valve assembly of claim 1, wherein the second end of the cannula is received within the first cylindrical portion when the valve sleeve is in the pre-use position.

10. A drug delivery device comprising:

a housing;

a container received within the housing, the container having a first end and a second end positioned opposite the first end, the container comprising a barrel having a first end and a second end positioned opposite the first end of the barrel, the barrel configured to receive a medicament, a stopper moveable within the barrel to dispense the medicament from the barrel, and a septum received by the second end of the barrel and having a first side and a second side positioned opposite the first side, the container defining an open space extending from the second side of the septum to the second end of the container;

a drive assembly received within the housing and configured to engage the container and dispense medicament from the container;

a needle actuator assembly received within the housing, the needle actuator assembly comprising a patient needle configured to pierce a patient's skin; and a valve assembly comprising:

a valve housing having a first side and a second side positioned opposite from the first side;

a cannula having a first end and a second end positioned opposite the first end, the cannula defining a central passageway; and a valve sleeve defining a cannula space, the valve sleeve is configured to move from a pre-use position where the first end of the cannula is received within the cannula space to a use position where the first end of the cannula extends outside of the valve sleeve and the cannula space, wherein the valve sleeve is configured to contact a container of the drug delivery device before any other element of the valve assembly when the valve sleeve moves from the pre-use position to the use position.

11. The drug delivery device of claim 10, wherein the valve sleeve engages the septum of the container when the valve sleeve moves from the pre-use position to the use position.

12. A method of packaging and sterilizing the drug delivery device of claim 10, the method comprising:

a) sterilizing and positioning the barrel and septum of the container in a first package;

b) sterilizing and positioning the stopper of the container in a second package;

c) sterilizing and positioning the housing, the drive assembly, the needle actuator assembly, and the valve assembly in at least a third package;

d) filling the container with medicament;

e) completing final assembly of the drug delivery device and positioning the drug delivery device in a fourth package; and f) after step e), sterilizing the assembled drug delivery device.

13. The method of claim 12, wherein the sterilizing of step f) comprises a vaporized peracetic acid sterilization process.

14. The method of claim 12, wherein the fourth package comprises a porous material.

15. A drug delivery device comprising:

a housing;

a container received within the housing, the container having a first end and a second end positioned opposite the first end, the container comprising a barrel having a first end and a second end positioned opposite the first end of the barrel, the barrel configured to receive a medicament, a stopper moveable within the barrel to dispense the medicament from the barrel, and a septum received by the second end of the barrel and having a first side and a second side positioned opposite the first side, the container defining an open space extending from the second side of the septum to the second end of the container;

a drive assembly received within the housing and configured to engage the container and dispense medicament from the container;

a needle actuator assembly received within the housing, the needle actuator assembly comprising a patient needle configured to pierce a patient's skin; and a valve assembly comprising:

a valve housing having a first side and a second side positioned opposite from the first side;

a cannula having a first end and a second end positioned opposite the first end, the cannula defining a central passageway; and a valve sleeve defining a cannula space, the valve sleeve is configured to move from a pre-use position where the first end of the cannula is received within the cannula space to a use position where the first end of the cannula extends outside of the valve sleeve and the cannula space, wherein the valve sleeve is configured to contact a container of the drug delivery device before any other element of the valve assembly when the valve sleeve moves from the pre-use position to the use position, wherein the container further comprises a locking element having a main body and a locking ring, the locking element configured to secure the septum to the barrel of the container.

* * * * *